United States Patent
Rifkin et al.

(10) Patent No.: US 10,646,510 B2
(45) Date of Patent: *May 12, 2020

(54) AERATED CONFECTIONARIES COMPRISING SHELF-STABLE ACTIVE INGREDIENTS

(71) Applicant: Eclaire Farm, LLC, Vancouver, WA (US)

(72) Inventors: Martin Rifkin, Vancouver, WA (US); Charles Bedell, Vancouver, WA (US)

(73) Assignee: Eclaire Farm, LLC, Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/421,752

(22) Filed: Feb. 1, 2017

(65) Prior Publication Data

US 2017/0258918 A1   Sep. 14, 2017

Related U.S. Application Data

(63) Continuation-in-part of application No. 15/141,055, filed on Apr. 28, 2016, now abandoned, which is a continuation-in-part of application No. 15/068,544, filed on Mar. 12, 2016, now abandoned.

(51) Int. Cl.

| | |
|---|---|
| *A23G 3/36* | (2006.01) |
| *A61K 33/00* | (2006.01) |
| *A23G 3/52* | (2006.01) |
| *A23G 3/42* | (2006.01) |
| *A23G 3/54* | (2006.01) |
| *A23L 33/125* | (2016.01) |
| *A23L 33/15* | (2016.01) |
| *A23L 33/16* | (2016.01) |
| *A61K 31/593* | (2006.01) |
| *A61K 31/4045* | (2006.01) |
| *A61K 9/00* | (2006.01) |
| *A23L 33/10* | (2016.01) |
| *A61K 33/06* | (2006.01) |
| *A23L 33/175* | (2016.01) |
| *A61K 45/06* | (2006.01) |

(52) U.S. Cl.
CPC ............... *A61K 33/00* (2013.01); *A23G 3/36* (2013.01); *A23G 3/362* (2013.01); *A23G 3/364* (2013.01); *A23G 3/368* (2013.01); *A23G 3/42* (2013.01); *A23G 3/52* (2013.01); *A23G 3/54* (2013.01); *A23L 33/10* (2016.08); *A23L 33/125* (2016.08); *A23L 33/15* (2016.08); *A23L 33/16* (2016.08); *A23L 33/175* (2016.08); *A61K 9/0056* (2013.01); *A61K 31/4045* (2013.01); *A61K 31/593* (2013.01); *A61K 33/06* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,582,709 A | 4/1986 | Peters et al. |
| 6,673,380 B2 | 1/2004 | Yang et al. |
| 6,773,744 B1 * | 8/2004 | Ward ..................... A23G 3/34 426/658 |
| 7,022,356 B2 | 4/2006 | Schmidt |
| 8,597,703 B2 | 12/2013 | Boghani et al. |
| 2007/0275119 A1 | 11/2007 | Lakkis |
| 2008/0187621 A1 | 8/2008 | Boghani et al. |
| 2009/0175982 A1 | 7/2009 | Boghani et al. |
| 2011/0171342 A1 * | 7/2011 | Phillips, III ............ A23G 3/36 426/2 |
| 2013/0287899 A1 * | 10/2013 | Rifkin ................... A23L 29/212 426/72 |
| 2013/0316050 A1 | 11/2013 | Lincoln et al. |
| 2014/0087024 A1 * | 3/2014 | Khatib .................... A23G 3/52 426/61 |
| 2014/0186491 A1 | 7/2014 | Firrell et al. |

* cited by examiner

*Primary Examiner* — Jessica Worsham

(74) *Attorney, Agent, or Firm* — Mohr Intellectual Property Law Solutions, PC

(57) ABSTRACT

In one embodiment, a confectionary comprises at least one sweetener, at least one stabilizer, at least one emulsifier, water, a first active ingredient, and an enrobing layer. The water may comprise 2 to 20 wt. % of the confectionary. The confectionary may have a water activity of from 0.45 to 0.65. The confectionary may be aerated such that the density of the confectionary is 0.7 to 1.25 grams per cubic centimeter. The confectionary may have a pH of 5.0 to 8.0.

21 Claims, No Drawings

AERATED CONFECTIONARIES COMPRISING SHELF-STABLE ACTIVE INGREDIENTS

CROSS REFERENCE TO RELATED APPLICATIONS

This application claims priority to and is a continuation-in-part of copending U.S. application Ser. No. 15/068,544, filed on Mar. 12, 2016, which is hereby incorporated by reference for all purposes.

BACKGROUND

The present disclosure relates generally to delivery systems for vitamins, supplements, therapeutic pharmaceutical compounds and other such active ingredients. In particular, edible delivery systems for active ingredients are described.

Known delivery systems for vitamins and other active ingredients are not entirely satisfactory for the range of applications in which they are employed. For example, some users may have difficulty swallowing conventional active ingredient delivery systems such as pills or capsules. While there are some examples of conventional edible vitamins, these conventional edible vitamins may be difficult and unpleasant to eat, due at least in part to their size and dense chalky texture. Furthermore, the texture of non-aerated gelatin and pectin based vitamins may limit the amount of active ingredients that can be added.

Additionally, the active ingredients in known delivery systems may have a shorter shelf life than those in the delivery system contemplated herein, due at least in part to the effects of moisture, oxygen, light, heat and acidity on the active ingredients, and, the causing degradation of the active ingredients.

Finally, some active ingredients may have a strong salty and/or bitter taste. Known delivery systems for these active ingredients fail to overcome the bitter/salty taste, resulting in a delivery system that is unpleasant to eat.

Thus, there exists a need for edible delivery systems for active ingredients that improve upon and advance the design of known edible delivery systems for active ingredients. Examples of new and useful edible delivery systems for active ingredients relevant to the needs existing in the field are discussed below.

SUMMARY

In one embodiment, a confectionary comprises at least one sweetener, at least one stabilizer, water, and a first active ingredient. The water may comprise 2 to 20 wt. % of the confectionary. The aerated confectionary may have a water activity of from 0.45 to 0.65. The confectionary may be aerated such that the density of the confectionary is 0.7 to 1.25 grams per cubic centimeter.

DETAILED DESCRIPTION

The disclosed edible delivery systems for active ingredients will become better understood through review of the following detailed description. The detailed description provides merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various edible delivery systems for active ingredients are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

In some embodiments, the edible delivery system for active ingredients may take the form of a shelf-stable aerated confectionary. In general an aerated confectionary in accordance with the present invention comprises a sweetener, at least one stabilizer, at least one emulsifier, water, a first active ingredient, and an enrobing layer. The confectionary may be aerated, thus it may comprises air and/or other inert gas. For example the confectionary may comprise air trapped in small pores or pockets within the confectionary.

In some embodiments, the aerated confectionary may be a slabbed, aerated confectionary. As used herein, "slabbed" means a confectionary that has been spread out to uniform thickness in a frame or pan to be cut after it has set. In some embodiments, the aerated confectionary may be a grained aerated confectionary comprising, for example, 5 to 10 wt. % water.

In one embodiment, the confectionary may comprise 30 to 85 wt. % sweeteners. Any one (or more than one) of a large number of sweeteners may be used in the confectionary. As used herein, a sweetener is a substance that sweetens. Sweeteners include and sometimes consist of: sugar, sucrose, corn syrup, sorbitol, glucose, fructose, dextrose, agave nectar, stevia, sucralose, SPLENDA, monk fruit, honey, molasses, allulose, erythritol, xylitol, sorbitol, maltitol, polydextrose, aspartame, acesulfame potassium, saccharin, alitame, and tagatose. The aerated confectionary may further comprise coloring and/or flavoring.

As described above, an aerated confectionary in accordance with the present invention may comprise one or more stabilizers. The stabilizer may function to help form and retain the pores or pockets of gas within the confectionary. In some embodiments, the aerated confectionary may comprise not greater than 10 wt. % stabilizers. As used herein, a "stabilizer" means an edible material that functions to form pockets or pores in an aerated confectionary. Stabilizers include and sometimes consist of: milk protein, egg albumen, casein, and soya.

In some embodiments, the stabilizer may comprise one or more whipping agents, such as modified milk protein, egg albumen, skimmed milk (in spray or dried form), whey, casein, and soya.

In some embodiments, the egg albumen may be heated prior to being mixed into the confectionary. Heating the egg albumen may cause at least some of the proteins therein to denature. The denatured proteins may create a more stable texture and thus extend the shelf life of the aerated confectionary.

The aerated confectionary may be aerated via any method, including chemical aeration and/or mechanical aeration. Methods of mechanical aeration in accordance with the present invention include mixing via a planetary beater, batch pressure beater or continuous pressure beater and/or aeration via a pulling machine.

In some embodiments, the confectionary may be aerated in a pressurized chamber. In these embodiments, the density of the aerated confectionary may be controlled via controlling the duration and/or pressure of the pressurized chamber aeration. Higher pressure may result in smaller, more uniform formation of bubbles within the aerated confectionary. For example, in some embodiments, pressurized chamber aeration at approximately 60 psi may result in small bubbles and thus lead to a relatively firm and dense aerated confectionary. Conversely, lower pressure may result in larger, less uniform formation of bubbles within the aerated confectionary. In some embodiments, the aerated confectionary may be extruded after the pressurized chamber aeration step.

Due at least in part to the aeration, the aerated confectionary may have a relatively low density. For example, in one embodiment, the aerated confectionary may have density of 0.7 to 1.25. In other embodiments, aerated confectionary may have a density of not greater than 0.75. In other embodiments, aerated confectionary may have a density of not greater than 0.90. In other embodiments, aerated confectionary may have a density of not greater than 1.05. In other embodiments, aerated confectionary may have a density of not greater than 1.20.

As described above, an aerated confectionary in accordance with the present invention comprises water. In some embodiments, the water-related properties of the aerated confectionary may be critical to the long shelf-life of the active ingredients. Specifically, the water content and especially the water activity of the aerated confectionary may, at least in part, control the shelf life of the active ingredients. In some embodiments, lower water activity may extend the shelf life of the active ingredients. Similarly, low water content may extend the shelf like of the active ingredients.

As used herein, water content means the portion of the aerated confectionary that is water, as measured by weight percent (wt. %). As used herein, water activity means the ratio of the vapor pressure of water in an aerated confectionary to the vapor pressure of pure water at the same temperature.

In some embodiments, the aerated confectionary may comprise 2 to 20 wt. % water. In other embodiments, the aerated confectionary may comprise not greater than 18 wt. % water. In other embodiments, the aerated confectionary may comprise not greater than 16 wt. % water. In other embodiments, the aerated confectionary may comprise not greater than 14 wt. % water.

In some embodiments, the aerated confectionary may have a water activity of 0.45 to 0.65. In other embodiments, the aerated confectionary may have a water activity of not greater than 0.65. In other embodiments, the aerated confectionary may have a water activity of not greater than 0.60. In other embodiments, the aerated confectionary may have a water activity of not greater than 0.55. In other embodiments, the aerated confectionary may have a water activity of not greater than 0.50. In other embodiments, the aerated confectionary may have a water activity of not greater than 0.45.

In some embodiments the aerated confectionary may have a pH of 5.0 to 8.0. In other embodiments, the aerated confection may have a pH of not greater than 5.0. In other embodiments, the aerated confection may have a pH of not greater than 6.0. In other embodiments, the aerated confection may have a pH of not greater than 7.0. In other embodiments, the aerated confection may have a pH of not greater than 8.0.

As described above, an aerated confection in accordance with this present invention has a more neutral pH. In some embodiments, the pH related properties of the aerated confectionary may be critical to the long shelf-life of the active ingredients. Specifically, the pH of the aerated confectionary may, at least in part, control the shelf life of the active ingredients. Many active ingredients are more stable and less susceptible to oxidation at a neutral pH than at an acidic pH or an alkaline pH.

The aerated confectionary may be a shelf stable emulsion of water soluble and fat soluble active ingredients. The emulsification of the aerated confectionary may be critical to the long shelf-life of the active ingredients. Specifically, emulsification may, at least in part, control the shelf life of the active ingredients. During the process of emulsification, the water soluble active ingredients and the fat soluble active ingredients bind, and are isolated and suspended within the aerated confectionary, making them less susceptible to oxidation. The aerated confectionary may contain egg as the emulsifier. Other delivery systems, such as the non-aerated gelatin and pectin based candies are not stable emulsifications, but are rather an admixture of components.

The aerated confectionary may contain metal chelators. Chelation of the aerated confectionary may be critical to the long shelf-life of the active ingredients. Specifically, chelation may, at least in part, control the shelf life of the active ingredients. Transition metal ions and copper are known to accelerate the oxidation of nutrients. Through the process of chelation, the metal ions in the aerated confectionary are sequestered and inactivated when bound to a chelator. The aerated confection may contain egg white protein (albumin) and/or milk protein (casein), both known and effective chelators.

As described above, an aerated confectionary in accordance with the present invention comprises at least one active ingredient. As used herein, "active ingredient" means a dietary supplement or pharmaceutical compound. A pharmaceutical compound may be an over-the-counter drug or a prescription drug.

As used herein, "dietary supplement" means a substance intended to add further nutritional value to the diet and not considered food. A "dietary supplement" may be one, or a combination, of the following substances: a vitamin, a mineral, an herb and/or other botanical, an amino acid and/or protein, a fatty acid, an antioxidant, soluble and/or insoluble fiber, a digestive enzyme, a probiotic, a prebiotic, a micronutrient, a macronutrient, a metabolite, an extract, or any other supplements digested to promote the health and well-being of a person.

As used herein, "vitamin" includes and sometimes consists of: Vitamin A, B1 (Thiamine), B2 (Riboflavin), B3 (Niacin), B5 (Pantothenic Acid), B6, B7 (Biotin), B9 (Folic Acid), B12, Choline, C, D, E, K, Bioflavonoids, Coenzyme Q10, Inositol, and PABA (Para-Aminobenzoic Acid), and the like, in liquid or powder form.

As used herein, "Mineral" includes, and sometimes consists of: Calcium, Chromium, Copper, Iodine, Iron, Magnesium, Manganese, Molybdenum, Phosphorus, Potassium, Selenium, Zinc, and the like, in liquid or powder form.

As used herein "fatty acid" includes, and sometimes consists of: omega-3 ALA (Alpha Linolenic Acid), EPA (Eicosapentaenoic Acid), DHA (Docosahexaeonic Acid), omega-6, and omega-9.

As used herein, "dietary supplement" includes, and sometimes consists of one or more of the following. Acai Berry Extract, Aloe Powder, Althea Root (Marshmallow), Apple Fiber Powder, Astragalus Root, Barley Grass, Bee Pollen Powder, Beta Carotene, Betatene, Billberry Extract, Bing Cherry Powder, Biofirm, Black Cohosh, Black Currant Extract, Blackberry Powder, Blueberry Powder, Boron (Boron Citrate), Broccoli Powder, Bromelain, Burdock Root, Cabbage Powder, Caffeine (Caffeine Anhydrous), Calcium (Calcium Ascorbate), Calcium (Calcium Carbonate), Calcium (Calcium Gluconate), Calcium (Calcium Lactate), Calcium (Calcium Silicate), Calcium Citrate, Carrot Powder, Cauliflower Powder, Chamomile Extract, Chlorella, Choline (Choline Bitartrate), Choline (Choline Chloride), Chondroitin Sulfate, Chromium (Chromium Chelate), Chromium (Chromium Picolinate), Cinnamon Bark, Citrus Bioflavanoid, Coconut Oil (deoderized), Coffeeberry Powder, Collagen Peptides, Copper Chelate, CoQ10, Cranberry Powder, Echinacea Power, Elderberry Powder, Fiber (Fibersol), Fiber (Frutalose), Fiber (Polydextrose), Fiber (Raftilose), Flaxseed, GABA, Gamma Oryzanol, Ginkgo Biloba Powder, Ginseng (Korean Red Ginseng), Glucaosmine (Glucosamine HCl), Glucosamine Sulfate, Grape Seed Extract, Guarana Extract, I-Cysteine, IGlutamine, I-Glycine, I-Isoleucine, I-Leucine, I-Lycine, I-Methionine, Inosine, Inositol (Inositol Nicotinate), Iodine (Potassium Iodide), Iron, I-Taurine, I-Tyrosine, I-Valine, Kale Powder, Kelp Powder, Kola Nut, L-Carnitine, Lemon Balm Extract, Lemon Grass Powder, L-Glutamine, LLysine, L-Taurine, L-Theanine, L-Tyrosine, Lutein, Lutein (Floraglo), Lycopene (Lyconat), Lycopene (Redivivo), Magnesium (Gluconal Magnesium), Magnesium (Magnesium Aspartate), Magnesium (Magnesium Citrate), Maitake Powder, Manganese (Manganese Amino Acid Chelate), Manganese (Manganese Sulfate), Mango Powder, Mangosteen Extract, Mate Extract, Melatonin, Molybdenum (Molbdenum Citrate), N-Acetyl-L-Cysteine, Natural Egg Shell Membrane, Nickel (Nickel Amino Acid Chelate), Oat Straw Extract, Orange Crystals, Papain, *Papaya* Powder, Passion Flower Extract, Peptan, Phaseolamin, Phytosterols (Emulsified), Pineapple Powder, Pomegranate Powder, Potassium (Potassium Ascorbate), Potassium (Potassium Iodide), Probiotic Powder, Prune Powder, Psyllium Seed Husks, Rosehips, Salt, Sea Buckthorn Powder, Selenium (Amino Acid Chelate), Selenium (Sodium Selenate), Shephards Purse, Slippery Elm Bark, Spinach Powder, Spirulina Powder, Strawberry Powder, Sweet Apple Powder, Tomato Powder, Vanadium (Vanadium Citrate), Vitaberry Powder, Vitamin A Palmitate (Retinol), Vitamin B1 (Thiamin Mononitrate), Vitamin B1 Encapsulated (Thiamin), Vitamin B12 (Cobalamin), Vitamin B2 (Riboflavin), Vitamin B2 Encapsulated (Riboflavin), Vitamin B3 (Niacin), Vitamin B3 (Niacinamide), Vitamin B5 (Calcium Pantothenate), Vitamin B6 (Pyridoxal Phosphate), Vitamin B6 Encapsulated (Pyrodoxil Phosphate), Vitamin B7 (Biotin), Vitamin B9 (Folic Acid), Vitamin C (Ascorbic Acid), Vitamin C (Calcium Ascorbate), Vitamin C (Potassium Ascorbate), Vitamin C (Sodium Ascorbate), Vitamin D3 (Ergocalciferol), Vitamin E (Novatol), Vitamin E Acetate (Alpha Tocopherol), Vitamin K1, Wellberry Fruit Extract, Wheat Grass Powder, White Willow, Wild Yam Root Powder, Xylitol, Zinc (Zinc Citrate Dihydrate), Zinc (Zinc Gluconate), Zinc Sulfate, omega-3 Oil (Algae), omega-3 Oil (Chia Seed), omega-3 Oil (Fish), omega-3 Oil (Flaxseed), omega-3 Powder (Fish), omega-6, and omega-9.

As used herein, "pharmaceutical compound" or "drug" means any drug, hormone, peptide, nucleotide, antibody, or other chemical or biological substances used in treatment and prevention of diseases or illness, or substances which affect the structure or function of the body.

As used herein, "pharmaceutical compound" means a prescription or over the counter drug." Pharmaceutical compounds include, and sometimes consist of: an opioid analgesic agent (e.g., as morphine, hydromorphone, oxymorphone, levophanol, methadone, meperidine, fentanyl, codeine, hydrocodone, oxycodone, propoxyphene, buprenorphine, butorphanol, pentazocine and nalbuphine); a non-opioid analgesic agent (e.g., acetylsalicylic acid, acetaminophen, ibuprofen, ketoprofen, indomethacin, diflunisol, naproxen, ketorolac, dichlophenac, tolmetin, sulindac, phenacetin, piroxicam, and mefamanic acid); an anti-inflammatory agent (e.g., glucocorticoids such as alclometasone, fluocinonide, methylprednisolone, triamcinolone and dexamethasone; and nonsteroidal anti-inflammatory drugs such as celecoxib, deracoxib, ketoprofen, lumiracoxib, meloxicam, parecoxib, rofecoxib, and valdecoxib); an antitussive agent (e.g., dextromethorphan, codeine, hydrocodone, caramiphen, carbetapentane, and dextromethorphan); an antipyretic agent (e.g., acetylsalicylic acid and acetaminophen); an antibiotic agent (e.g., aminoglycosides such as, amikacin, gentamicin, kanamycin, neomycin, netilmicin, streptorycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cetprozil, cefuroxime, cetftazidime, cefdinir, cefditoren, cetoperazone, cefotaxime, cetpodoxime, ceftazidime, ceftibuten, ceftizoxime, and ceftriaxone; macrolides such as azithromycin, clarithromycin, dirithromycin, erythromycin and troleandomycin; monobactam, penicillins such as amoxicillin, ampicillin, carbenicillin, cloxacillin, dicioxacillin, nafilcillin, oxacillin, penicilin G, penicillin V, piperacillin, and ticarcillin; polypeptides such as bacitracin colstin, and polymycin B; quinolones such as ciprofloxacin, enoxacin, gatifloxacin, levofloxacin, ometloxacin, moxfolxacin, norfloxacin, ofloxacin and trovatioxacin, sulfonamides such as mafenide sulfacetamide, sulfamethizole, sulfasalazine, sulfisoxazole, and trimethoprim-sulfamethoxazole; and tetracyclines such as demeclocycline, doxycycline, minocycine, and oxytetracycline); an antimicrobial agent (e.g., ketoconazole, amoxicillin, cephalexin, miconazole, econazole, acyclovir, and nelfinavir); a steroidal agent (e.g., estradiol, testosterone, cortisol, aldosterone, prednisone, and cortisone); an amphetamine stimulant agent (e.g., amphetamine); a non-amphetamine stimulant agent (e.g., methylphenidate, nicotine, and caffeine); a laxative agent (e.g., bisacodyl, casanthranol, *senna*, and castor oil); an anorexic agent (e.g., fenfluramine, dexfenfluramine, mazindol, phentermine, and aminorex); an antihistaminic agent (e.g., phencarol, cetirizine, cinnarizine, ethamidindole, azatadine, brompheniramine, hydroxyzine, and chlorpheniramine); an antiasthmatic agent (e.g., zileuton, montelukast, omalizumab, fluticasone, and zafirlukast); an antidiuretic agent (e.g., desmopressin, vasopressin, and lypressin); an antiflatulant agent (e.g., simethicone); an antimigraine agent (e.g., naratriptan, frovatriptan, eletriptan, dihydroergotamine, zolmitriptan, almotriptan, and sumatriptan); an antispasmodic agent (e.g., dicyclomine, hyoscyamine, and peppermint oil); an antidiabetic agent (e.g., methformin, acarbose, miglitol, pioglitazone, rosiglitazone, troglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); an antacid (e.g., aluminium hydroxide, magnesium hydroxide, calcium carbonate, sodium bicarbonate, and bismuth subsalicylate); a respiratory agent (e.g., albuterol, ephedrine, metaproterenol, and terbutaline); a sympathomimetic agent (e.g., pseudoephedrine, phenylephrine, phenylpropanolamine, epinephrine, norepinephrine, dopamine, and ephedrine); an H2 blocking agent (e.g., cimetidine, famotidine, nizatidine, and ranitidine); an antihyperlipidemic agent (e.g., clofibrate, cholestyramine, colestipol, fluvastatin, atorvastatin, genfibrozil, lovastatin, niacin, pravastatin, fenofibrate, colesevelam, and simvastatin); an antihypercholesterol agent (e.g., lovastatin, simvastatin, pravastatin, fluvastatin, atorvastatin, cholestyramine, colestipol, colesevelam, nicotinic acid, gemfibrozil, and ezetimibe); a cardiotonic agent (e.g., digitalis, ubidecarenone, and dopamine); a vasodilating agent (e.g., nitroglycerin, captopril, dihydralazine, diltiazem, and isosorbide dinitrate); a vasocontricting agent (e.g., dihydroergotoxine and dihydroergotamine); a sedative agent (e.g., amobarbital, pentobarbital, secobarbital, clomethiazole, diphenhydramine hydrochloride, and alprazolam); a hypnotic agent (e.g., zaleplon, zolpidem, eszopiclone, zopiclone, chloral hydrate, and clomethiazole); an anticonvulsant agent (e.g., lamitrogene, oxycarbamezine, pheytoin, mephenytoin, ethosuximide, methsuccimide, carbamazepine, valproic acid, gabapentin, topiramate, felbamate, and phenobarbital); a muscle relaxing agent (e.g., baclofen, carisoprodol, chlorzoxazone, cyclobenzaprine, dantrolene sodium, metaxalone, orphenadrine, pancuronium bromide, and tizanidine); an antipsychotic agent (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); an antianxiolitic agent (e.g., lorazepam, alprazolam, clonazepam, diazepam, buspirone, meprobamate, and flunitrazepam); an antihyperactive agent (e.g., methylphenidate, amphetamine, and dextroamphetamine); an antihypertensive agent (e.g., alphamethyldopa, chlortalidone, reserpine, syrosingopine, rescinnamine, prazosin, phentolamine, felodipine, propanolol, pindolol, labetalol, clonidine, captopril, enalapril, and lisonopril); an anti-neoplasia agent (e.g., taxol, actinomycin, bleomycin A2, mitomycin C, daunorubicin, doxorubicin, epirubicin, idarubicin, and mitoxantrone); a soporific agent (e.g., zolpidem tartrate, eszopiclone, ramelteon, and zaleplon); a tranquilizer (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); a decongestant (e.g., ephedrine, phenylephrine, naphazoline, and tetrahydrozoline); a beta blocker (e.g., levobunolol, pindolol, timolol maleate, bisoprolol, carvedilol, and butoxamine); an alpha blocker (e.g., doxazosin, prazosin, phenoxybenzamine, phentolamine, tamsulosin, alfuzosin, and terazosin); a non-steroidal hormone (e.g., corticotropin, vasopressin, oxytocin, insulin, oxendolone, thyroid hormone, and adrenal hormone); a herbal agent (e.g., glycyrrhiza, aloe, garlic, nigella sativa, rauwolfia, St John's wort, and valerian); an enzyme (e.g., lipase, protease, amylase, lactase, lysozyme, and urokinase); a humoral agent (e.g., prostaglandins, natural and synthetic, for example, PGE1, PGE2alpha, and PGF2alpha, and the PGE1 analog misoprostol); a psychic energizer (e.g., 3-(2-aminopropy)indole and 3-(2-aminobutyl)indole); a vitamin (e.g., retinol, retinal, retinoic acid, 3-dehydroretinol, thiamine, riboflavin, niacin, pantothenic acid, pyridoxine, biotin, folic acid, cyanocobalamin, ascorbic acid, lumisterol, ergocalciferol, cholecalciferol, dihydrotachysterol, tocopherol, and naphthoquinone); a mineral (e.g., calcium, iron, zinc, selenium, copper, iodine, magnesium, phosphorus, and chromium); an anti-nausea agent (e.g., dolasetron, granisetron, ondansetron, tropisetron, meclizine, and cyclizine); a hematinic agent (e.g., ferrous salts, ferrous amino chelates, ferrous sulfate, ferrous fumarate, Ferrochel iron); a nutritional product (e.g., bee pollen, bran, wheat germ, kelp, cod liver oil, ginseng, and fish oils, amino acids, proteins, and mixtures thereof); and a fiber product (e.g., stabilizing, lignin, polydextrose, prebiotics, waxes, chitins, pectins, beta-glucans, inulin, and oligosaccharides.

OTCs may include any of the following brand name or generic equivalent drugs: BENADRYL®, SUDAFED®, CLARITIN®, MAALOX®, MYLANTA®, INSULIN, TUMS®, PEPCID® AC, MONISTAT®, EX-LAX®, IMODIUM® A.D., ROBITUSSIN®, CHLORASEPTIC®, THERA-FLU®, ALKA-SELTZER, MOTRIN®, DRAMAMINE®, and the like, in liquid or powder form.

A pharmaceutical compound may include a prescription drug. Such prescription drugs such may include brand name or generic forms of LIPITOR®, SINGULAIR®, LEXAPRO, PLAVIX®, MORPHINE, HYDROCODONE (VICODIN®), DEMEROL®, CODEINE, DIAZEPAM (VALIUM®), PENICILLIN, PREVACID®, ALLEGRA-D®, CELEBREX®, CRESTOR®, CIALIS®, VALTREX®, VIAGRA®, CIALIS®, PRILOSEC®, LIPITOR®, AMBIEN CR®, VIAGRA®, FLOMAX®, PROZAC®, and the like, in liquid or powder form. In some embodiments, in addition to an active pharmaceutical ingredient, the active ingredients of the delivery system may also include a combination of dietary supplements. The inclusion of dietary supplements with pharmaceutical compounds will depend in part on the compatibility of the supplement with the pharmaceutical compound.

In some embodiments, the delivery system may further comprise a flavor layer. The flavor layer may at least partially envelope the above-described confectionaries. In this regard, the above-described confectionaries may be a base layer in relation to the flavor layer.

In some embodiments the flavor layer may comprise of caramel, nuts, nut butters, and or mint. In some embodiments the flavor layer may further comprise one or more of the above-described active ingredients.

In some embodiments, the water-related properties of the flavor layer may be critical to the long shelf-life of the active ingredients. Specifically, the water content and especially the water activity of the flavor layer may, at least in part, control the shelf life of the active ingredients within both the flavor layer and the aerated confectionary base layer. In some embodiments, lower water activity may extend the shelf life of the active ingredients. Similarly, low water content may extend the shelf like of the active ingredients.

In some embodiments, the flavor layer comprises caramel. In one embodiment, the caramel flavor layer may comprise 5 to 20 wt. % water. In other embodiments, the caramel flavor layer may comprise not greater than 15 wt. % water. In other embodiments, the caramel flavor layer may comprise not greater than 10 wt. % water.

In one embodiment, the caramel flavor layer may have a water activity of 0.4 to 0.58. In other embodiments, the flavor layer may have a water activity of not greater than 0.45. In other embodiments, the flavor layer may have a water activity of not greater than 0.50. In other embodiments, the flavor layer may have a water activity of not greater than 0.55.

In one embodiment, the caramel flavor layer may have a density of 1.0 to 1.5 grams per cubic centimeter. In other embodiments, the caramel flavor layer may have a density of not greater than 1.4 grams per cubic centimeter. In other embodiments, the caramel flavor layer may have density of not greater than 1.3 grams per cubic centimeter. In other embodiments, the flavor layer may have a density of not greater than 1.2 grams per cubic centimeter. In other embodiments, the flavor layer may have a density of not greater than 1.1 grams per cubic centimeter.

In some embodiments, the flavor layer may be used to mask the taste of bitter and or salty active ingredients. As described above, the active ingredient(s) may have a bitter and or salty taste. Non-limiting examples of salty active ingredients include calcium containing material, chondroitin, hyaluronic acid, glucosamine, magnesium sulfate, zinc sulfate, selenium, manganese sulfate, chromium sulfate, sodium containing material, potassium sulfate, boron, and electrolytes, to name a few. Non-limiting examples of bitter active ingredients include biotin, caffeine, amino acids and some OTCs, to name a few.

In some embodiments, the caramel flavor layer may comprise nuts.

In one embodiment, the confectionary may comprise an enrobing layer. The enrobing layer may fully envelop an aerated confectionary piece. Many active ingredients are susceptible to moisture, oxidation from air, and photo-degradation due to light exposure. In some embodiments, the enrobing layer may help to protect the active ingredients from degrading by maintaining optimal moisture content and/or water activity within the aerated confectionary piece by reducing off gassing of water. In some embodiments, the enrobing layer may help protect the active ingredients from degrading by limiting exposure to light and oxygen. In some embodiments, the enrobing layer may be porous, and in some embodiments, the enrobing layer may be nonporous, for example the enrobing layer may comprise a hard candy shell or a chocolate or yogurt coating.

In some embodiments, the enrobing layer comprises at least one sweetener and water. The moisture content of the enrobing layer may determine, at least in part, the ability of the enrobing layer to maintain optimal moisture content and/or water activity within the aerated confectionary center. The enrobing layer may further comprise coloring and or flavoring. In some embodiments, the enrobing layer may comprise one or more of the above described active ingredients.

In some embodiments, the water-related properties of the enrobing layer may be critical to the long shelf-life of the active ingredients. Specifically, the water content and especially the water activity of the enrobing layer may, at least in part, control the shelf life of the active ingredients within the enrobing layer, flavor layer and the aerated confectionary base layer. In some embodiments, lower water activity may extend the shelf life of the active ingredient. Similarly, low water content may extend the shelf life of the active ingredients.

In one embodiment, the enrobing layer comprises 0.1 to 6 wt. % water. In other embodiments, the enrobing layer comprises 0.1 to 4 wt. % water. In other embodiments, the enrobing layer comprises 0.1 to 3 wt. % water. In other embodiments, the enrobing layer comprises 0.1 to 2 wt. % water. In other embodiments, the enrobing layer comprises 0.1 to 1 wt. % water.

In some embodiments, the process for making the aerated confectionary takes advantage of the separate stages to minimize the degradation of active ingredients. There are three key stages to the process: (1) egg whip (cold), (2) syrup (hot), and (3) fat (warm). Of the three stages, active ingredients only come into contact with high heat in the syrup stage, and the active ingredients in this stage are only exposed to heat not greater than 124.5 degrees Celsius.

In some embodiments, the active ingredients may be incorporated into the aerated confectionary in a manner designed to minimize degradation of the active ingredient(s) and or improve the solubility of the active ingredients in the aerated confectionary. For example, B9 Folic Acid may be mixed into an unfinished confectionary mixture along with cold egg ingredients. As another example, liquid fat soluble Vitamin E may be mixed into an unfinished confectionary mixture along with one or more warm fats. Additional examples are shown in Tables 1-3 below:

TABLE 1

Hot Water Soluble Active Ingredients, added at the hot Syrup Mixture stage.

| Active (form) | Water | Heat | Air | Other | Interactions |
| --- | --- | --- | --- | --- | --- |
| B5 Pantothenic Acid (d-calcium pantothenate) | Freely soluble in water Protect from moisture Hygroscopic Hydrolytic Cleavage at high or low pH | | Moderately stable | Moderately stable to light Max pH range = 6-7 | |
| B9 Folic Acid May be added with egg ingredients since high heat & Ascorbic Acid degrades, but not very soluble in cold water | Very slightly soluble in cold water Soluble up to 1% in boiling water | Moderately stable Extra heat involved in boiling can lead to high degradation | Moderately stable to atmospheric oxygen | Stable pH 7 Increasing unstable with acid, particularly at pH <5 Sunlight (UV) very damaging | Ascorbic Acid - reduces B9 (rapidly in pH range 3.0-3.3, slower in pH range 6.5-6.7) Riboflavin - accelerate degradation Oxidizing & Reducing agents - accelerate degradation |
| B7 Biotin | More soluble in hot water | Stable in low acid Degrades in high acid or alkaline | Stable | Stable to daylight Gradually decompose by UV | Avdidin, protein in raw egg white, can inactivate |

TABLE 1-continued

Hot Water Soluble Active Ingredients, added at the hot Syrup Mixture stage.

| Active (form) | Water | Heat | Air | Other | Interactions |
|---|---|---|---|---|---|
| Vit C (calcium ascorbate) | Very soluble in water Readily oxidized in aqueous solutions Rate of degradation in aqueous solutions is pH dependent - Max = 4 pH | Considerable loss in cooking | Stable in dry air Significant effects of dissolved oxygen | Insoluble in fat Mfg with stainless steel, aluminum or plastic only Sensitive to sunlight or white fluorescent light Well preserved in condensed full milk cream (less oxygen than milk) | Phenolic substances in blackcurrant juices - protective Sequestrants (EDTA & cysteine) - reduce oxidation (optimal EDTA mole ratio 2.3) Heavy metal ions - degrade Cu & Fe - oxidize |

TABLE 2

Cold Water Soluble Active Ingredients, added at the cold Egg Whip Mixture stage.

| Active (form) | Heat | Air | Other | Interactions |
|---|---|---|---|---|
| B6 (pyridoxine hydrochloride) | Stable to heat Extra heat involved in boiling can lead to high degradation | Stable to atmospheric oxygen | Sensitive to light, especially sunlight | Metal ions - catalyze degradation |
| B12 (cyanocobalamin 1% on dcp) | Stable to heat Extra heat involved in boiling can lead to high degradation | Stable to atmospheric oxygen | Sensitive to light, especially UV | Oxidizing & Reducing agents - accelerate degradation Strong acids - breakdown Ascorbic Acid in aqueous solution - reduces B12 (rapidly when pH = 7, slower when pH <1) Significantly influenced by other vitamins |

TABLE 3

Fat Soluble Active Ingredients, added at the warm Fat Mixture stage.

| Active (form) | Heat | Air | Other | Interactions |
|---|---|---|---|---|
| Vit A (Retinyl Palmitate) | Stable | Sensitive to atmospheric oxygen | Catalyzed by presence of trace minerals | Vit E helps stabilize |
| Vit E - Natural (dl-alpha-tocopherol acetate) | Stable in heat in the absence of air Not stable in heat with the presence of air Reduced stability below freezing | Oxidized by air | | Metals (like iron) - Becomes pro-oxidant |

TABLE 3-continued

Fat Soluble Active Ingredients, added at the warm Fat Mixture stage.

| Active (form) | Heat | Air | Other | Interactions |
|---|---|---|---|---|
| Vit D3 (Cholecalciferol) | | Destroyed by atmospheric oxygen (more stable than D2) | Practically insoluble in water Slightly soluble in vegetable oil Soluble in organic solvents Destroyed in light Oil base Vit D more stable than crystalline | Acids - accelerate degradation |

In some embodiments, the aerated confectionary comprises at least one void formed with the confectionary and a filling placed in the void. The filling may comprise a sweetener and at least one of the above described active ingredients.

In one embodiment, the aerated confectionary may be injected with a pectin gel. The pectin gel may contain a desiccant, such as a silica desiccant. The desiccant may serve to maintain optimal moisture levels within the aerated confectionary.

In some embodiments, the confectionary may be packaged in a packaging that is not opaque in order limit the confections exposure to light and help to minimize the degradation of the active ingredients.

Example 1—Shelf-Stable Fortified Aerated Confectionary

A shelf-stable and vitamin-fortified aerated confectionary was prepared as follows. Egg white powder is hydrated in water with active ingredient, if any in this stage. Granulated white sugar is added to the water/egg mixture and whipped to a high peak (Egg Whip Mixture). Corn syrup, granulated white sugar, salt, and active ingredients, if any in this stage, are combined into a mixture and brought to 124.5 degrees Celsius to create a syrup (Syrup Mixture). Melted palm fat, confectioners' sugar, the emulsifier, cocoa powder, milk powder, flavoring and active ingredients, if any in this stage, are combined into a mixture (Fat Mixture). The Syrup Mixture is added to the Egg Whip Mixture on a high whip. The Fat Mixture is then slowly added and incorporated into the Egg Whip/Syrup Mixture. The resulting aerated confectionary mixture was slabbed, cut into 1 to 15 gram pieces, and then enrobed in compound chocolate.

Example 2—Shelf-Stable Calcium Fortified Aerated Confectionary

An aerated confectionary mixture was prepared in accordance with Example 1 using 23 g of egg white powder, 135 g of water, 427 g of granulated white sugar as the sweetener, 433 g of corn syrup, 1.5 g of kosher salt, 5 g of flavoring, 55 g of milk powder, 44 g of cocoa powder, 22 g of confectioners' sugar, 200 g of palm fat, 10 g of glycerolmonostearate as the emulsifier, and 50 g of calcium carbonate as the active ingredient. The resulting aerated confectionary mixture was then slabbed and cut into 1 to 15 gram pieces and enrobed in a compound chocolate coating to extend shelf life.

Example 3—Shelf-Stable Enrobed Vitamin D Fortified Aerated Confectionary

An aerated confectionary mixture was prepared in accordance with Example 1 using 18 g of egg white powder, 211 g of water, 492 g of granulated white sugar as the sweetener, 440 g of corn syrup, 1.5 g of kosher salt, 10 g of flavoring, 50 g of milk powder, 12 g of confectioners' sugar, 30 g of cocoa powder, 112 g of palm fat, 4.5 g of glycerolmonostearate as the emulsifier, and 5 g of vitamin D3 as the active ingredient. The resulting aerated confectionary mixture was then slabbed and cut into 1 to 15 gram pieces and enrobed in a compound chocolate coating to extend self-life.

Example 4—Shelf-Stable Enrobed Multi Vitamin Fortified Aerated Confectionary An aerated confectionary mixture was prepared in accordance with Example 1 using 18 g of egg white powder, 135 g of water, 492 g of granulated white sugar as the sweetener, 445 g of corn syrup, 1.5 g of kosher salt, 3 g of flavoring, 40 g of milk powder, 26 g of cocoa powder, 12 g of confectioners' sugar, 112 g of palm fat, 4.5 g of glycerolmonostearate as the emulsifier, and 62 g of a multi vitamin blend as the active ingredient. The resulting aerated confectionary mixture was then slabbed and cut in 1 to 15 gram pieces and enrobed in a compound chocolate coating to extend self-life.

Example 5—Shelf-Stable Enrobed Melatonin Fortified Aerated Confectionary

An aerated confectionary mixture was prepared in accordance with Example 1 using 18 g of egg white powder, 135 g of water, 492 g of granulated white sugar as the sweetener, 448 g corn syrup, 1.5 g of kosher salt, 2.5 g of flavoring, 40 g of milk powder, 26 g of cocoa powder, 11 g of confectioners' sugar, 112 g of palm fat, 4.5 g of glycerolmonostearate as the emulsifier, and 4.3 g of Melatonin as the active ingredient. The resulting aerated confectionary mixture was then slabbed and cut into 1 to 15 gram pieces and enrobed in a compound chocolate coating to extend self-life.

Example 6—Calcium Carrying Capacity of Non-Aerated Gelatin or Pectin Based Vitamin vs. Aerated Confectionary Several calcium fortified aerated confectionary samples were prepared in accordance with Example 2, however, the relative composition of calcium carbonate was varied in each sample. For comparison, several non-aerated gelatin and pectin based candies were mixed to contain calcium carbonate, wherein the relative composition of calcium carbonate was varied in each—non-aerated gelatin and pectin based sample. The non-aerated gelatin and pectin based samples comprising about 5 wt. % or more calcium were observed to be crumbly and fail to retain their molded shape. Conversely, the calcium carbonate fortified aerated confections were observed to achieve a much higher calcium carrying capacity than the non-aerated gelatin and pectin based candies. Specifically, the aerated confectionary samples comprising 33 wt. % or less calcium were observed to retain their texture and structure. Without wishing to be bound by theory, applicant postulates that aerated confectionaries have the ability to contain more active ingredients than other forms of confectionary products due at least in part to the pores and or bubbles present within the aerated confectionaries. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A confectionary, comprising:
an inner layer aerated such that a density of the confectionary is 0.75 to 1.25 grams per cubic centimeter, wherein the inner layer comprises:
a sweetener;
a stabilizer;
an emulsifier;
water comprising 2 to 20 wt. % of the confectionary; and;
a first active ingredient comprising vitamin A, vitamin B5, vitamin B6, vitamin B7, vitamin B9, vitamin B12, vitamin C, vitamin D, or vitamin E, wherein:
when the first active ingredient is the vitamin B5, the vitamin B7, or the vitamin C, the first active ingredient is added into and is mixed with a syrup during a syrup mixture stage to decrease a degradation of the first active ingredient;
when the first active ingredient is the vitamin B6, the vitamin B9, or the vitamin B12, the first active ingredient is added into and is mixed into confectionary with an egg ingredient during an egg whip stage to decrease a degradation of the first active ingredient;
when the first active ingredient is the vitamin A, the vitamin D, or the vitamin E, the first active ingredient is added into and is mixed into the confectionary with a fat during a fat mixture stage to decrease a degradation of the first active ingredient;
a continuous enrobing layer enveloping the inner layer; and
a metal chelator operable to extend a shelf-life of the first active ingredient;
wherein the sweetener comprises 30 to 85 wt. % of the confectionary,
wherein the confectionary has a pH of 5.0 to 8.0,
wherein the confectionary has a water activity of 0.45 to 0.65, and
wherein the first active ingredient has a decrease in degradation.

2. The confectionary of claim 1, wherein the sweetener comprises: sugar, sucrose, corn syrup, sorbitol, glucose, fructose, dextrose, agave nectar, stevia, sucralose, monk fruit compounds, honey, molasses, allulose, xylitol, sorbitol, maltitol, polydextrose, aspartame, acesulfame potassium, saccharin, or alitame.

3. The confectionary of claim 1, wherein the stabilizer comprises: milk protein, egg albumen, or casein.

4. The confectionary in claim 1, wherein the emulsifier comprises: glycerol monostearate, egg albumen, or milk protein.

5. The confectionary of claim 1, wherein the water comprises not greater than 12 wt. % of the confectionary.

6. The confectionary of claim 1, wherein the water activity is not greater than 0.60.

7. The confectionary of claim 1, further comprising a flavor layer.

8. The confectionary of claim 7, wherein the flavor layer comprises caramel, nuts, nut butter, or mint.

9. The confectionary of claim 8, wherein the flavor layer comprises 5 to 20 wt. % water.

10. The confectionary of claim 9, wherein the flavor layer has a water activity of 0.45 to 0.58.

11. The confectionary of claim 7, wherein the flavor layer comprises a second active ingredient.

12. The confectionary of claim 11, wherein the second active ingredient is a dietary supplement comprising: vitamin A, vitamin B2, vitamin B3, vitamin B5, vitamin B6, vitamin B7, vitamin B9, vitamin B12, vitamin C, vitamin D, or vitamin E.

13. The confectionary of claim 1, wherein the continuous enrobing layer is nonporous.

14. The confectionary of claim 13, wherein the continuous enrobing layer comprises another sweetener and another water.

15. The confectionary of claim 14, wherein the water of the continuous enrobing layer comprises 0.1 to 6 wt. % of the enrobing layer.

16. The confectionary of claim 14, wherein the water of the continuous enrobing layer comprises 0.1 to 2 wt. % of the enrobing layer.

17. The confectionary of claim 14, wherein the water of the continuous enrobing layer comprises 0.1 to 1 wt. % of the enrobing layer.

18. The confectionary of claim 14, wherein the water of the continuous enrobing layer has a water activity of 0.35 to 0.75.

19. The confectionary of claim 13, wherein the continuous enrobing layer comprises a second active ingredient.

20. The confectionary of claim 19, wherein the second active ingredient is a dietary supplement comprising: vitamin A, vitamin B12, vitamin B3, vitamin B5, vitamin B6, vitamin B7, vitamin B9, vitamin B12, vitamin C, vitamin D, or vitamin E.

21. The confectionary of claim 11 comprising:
a void formed within the confectionary; and
a filling disposed in the void, wherein the filling comprises another sweetener and a third active ingredient.

* * * * *